United States Patent [19]

Rubin

[11] Patent Number: 4,619,678

[45] Date of Patent: Oct. 28, 1986

[54] APPARATUS AND METHOD FOR TRANSPORTING AND PRESERVING PERISHABLE TEST SAMPLES

[76] Inventor: Howard Rubin, 1937 Nester St., Philadelphia, Pa. 19115

[21] Appl. No.: 754,615

[22] Filed: Jul. 12, 1985

Related U.S. Application Data

[63] Continuation of Ser. No. 563,560, Dec. 20, 1983, abandoned, which is a continuation of Ser. No. 375,018, May 5, 1983, abandoned.

[51] Int. Cl.⁴ .............................................. F25D 5/00
[52] U.S. Cl. .......................................... 62/4; 128/403
[58] Field of Search ...................... 62/4; 128/402, 403, 128/399, DIG. 26, DIG. 27; 206/219, 233

[56] References Cited

U.S. PATENT DOCUMENTS

| | | | |
|---|---|---|---|
| 1,549,510 | 8/1925 | Schnitzler | 128/403 |
| 2,756,874 | 7/1956 | Erickson et al. | 62/4 |
| 2,882,692 | 4/1959 | Robbins | 62/4 |
| 2,898,744 | 8/1959 | Robbins | 62/4 |
| 2,907,173 | 10/1959 | Robbins | 206/219 |
| 3,014,117 | 12/1961 | Madding | 128/403 X |
| 3,074,544 | 1/1963 | Bollmeier et al. | 206/219 |
| 3,149,943 | 9/1964 | Amador | 62/4 |
| 3,175,558 | 3/1965 | Caillouette et al. | 128/403 |
| 3,429,315 | 2/1969 | McDonald | 128/403 |
| 3,463,161 | 8/1969 | Andrassy | 128/402 |
| 3,545,230 | 8/1968 | Morse | 62/530 |
| 3,628,537 | 12/1971 | Berndt et al. | 128/403 X |
| 3,643,665 | 2/1972 | Caillouette | 128/403 |
| 3,674,134 | 7/1972 | Turner | 206/47 A |
| 3,763,622 | 10/1973 | Stanley, Jr. | 62/4 X |
| 3,804,077 | 4/1974 | Williams | 62/4 |
| 3,834,396 | 9/1974 | Foster | 128/403 |
| 3,874,504 | 4/1975 | Verakas | 206/219 |
| 3,887,346 | 6/1975 | Erdman | 62/4 |
| 3,893,834 | 7/1975 | Armstrong | 62/4 |
| 3,977,202 | 8/1976 | Forusz et al. | 62/4 |
| 3,986,834 | 10/1976 | Steinbrink, Jr. | 206/219 X |
| 4,049,408 | 9/1977 | Patel | 62/4 |

Primary Examiner—Frank Sever
Attorney, Agent, or Firm—Steele, Gould & Fried

[57] ABSTRACT

An apparatus for transporting and preserving perishable test samples, comprising: a pair of substantially flat leaf members foldably connected to one another; membranes disposed on each of the leaf members over a substantial portion thereof, forming reservoirs; a latent refrigerant disposed in the reservoir; and, at least one strip for gripping and holding the leaf members together to surround and cushion the test sample, and hold the test sample in heat exchanging relationship with the reservoirs, whereby upon activation of the latent refrigerant the test samples may be safely transported and preserved in a chilled environment. The leaf members and the membranes may be flat except for portions corresponding in shape to the test samples, the portions forming a pocket for receiving a test sample. The pocket may be formed by a holding strap disposed over one of the reservoirs. The leaf members may alternatively bear a clip member for holding the test sample.

A method for transporting and preserving perishable test samples, comprising the steps of: providing at least one of a pair of substantially flat leaf members, foldably connected to one another, with an integrally formed reservoir over a substantial portion thereof; filling the reservoir with a latent refrigerant; and, after a perishable test sample has been taken, activating the latent refrigerant; and, surrounding and cushioning the test sample with the reservoir and holding the test sample in heat exchanging relationship therewith, by closing the leaf members together over the test samples, whereby the test sample may be safely transported and preserved in a chilled environment.

14 Claims, 12 Drawing Figures

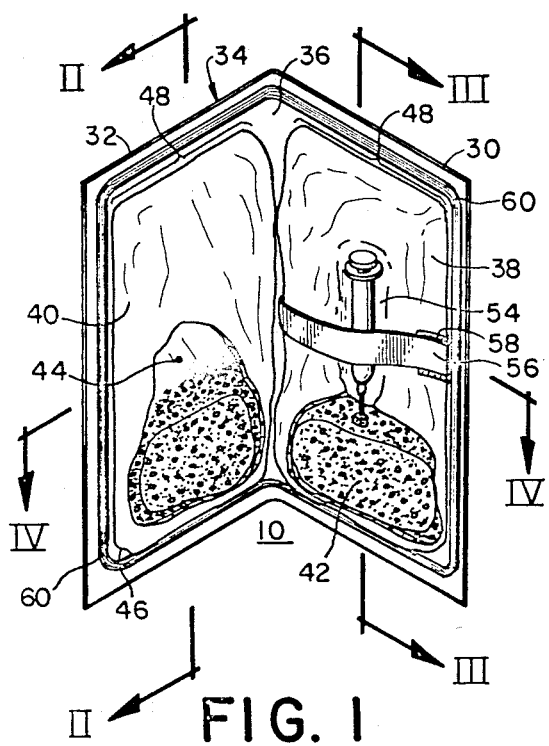
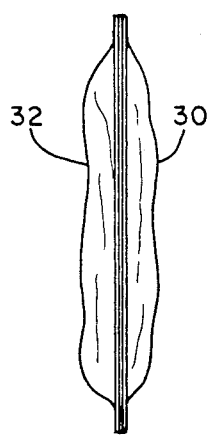
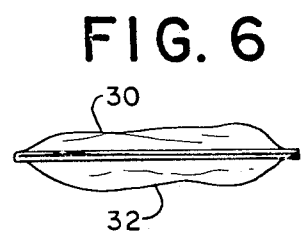
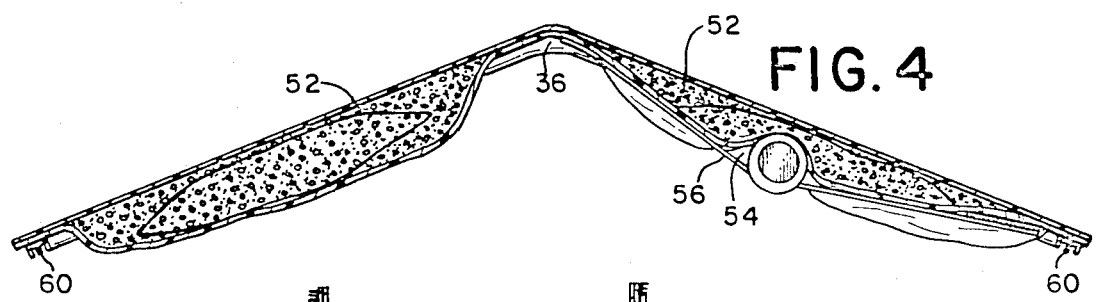
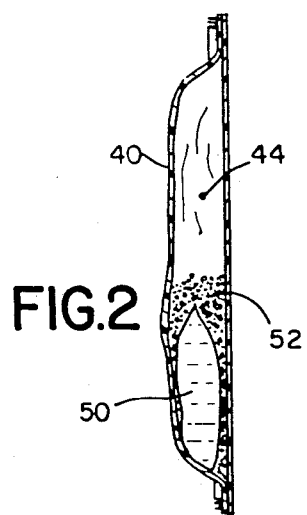
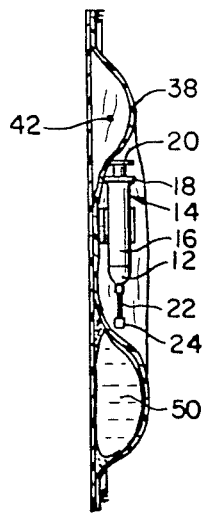

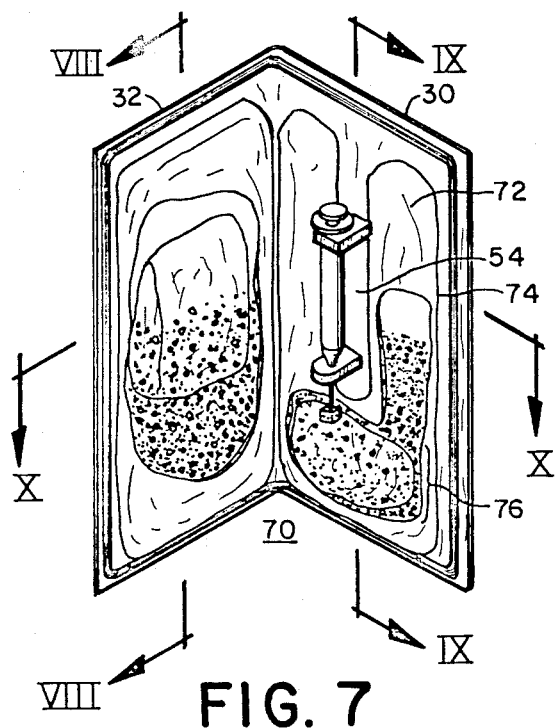
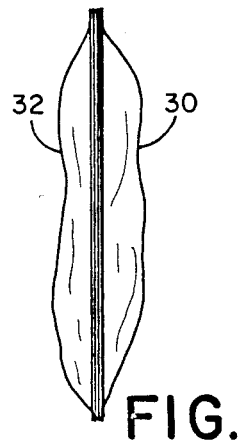
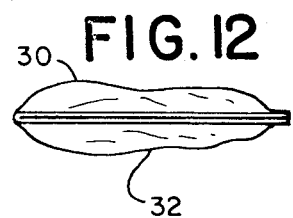
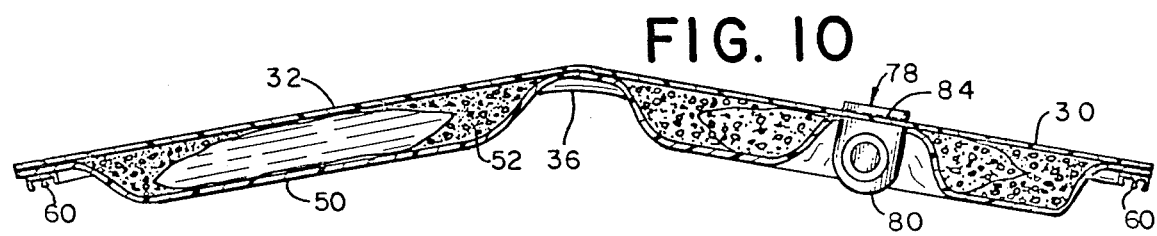
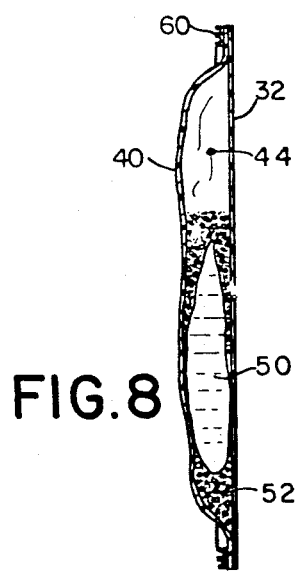
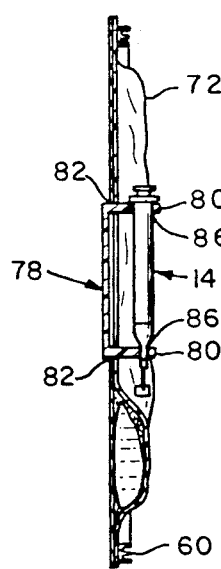

APPARATUS AND METHOD FOR TRANSPORTING AND PRESERVING PERISHABLE TEST SAMPLES

CROSS-REFERENCES TO RELATED APPLICATIONS

This application is a continuation of application Ser. No. 563,560, filed 12/20/83, now abandoned. Application Ser. No. 563,560 is a continuation of application Ser. No. 375,018, filed 05/05/83, now abandoned.

BACKGROUND OF THE INVENTION

1. Field of the Invention

This invention relates to the field of medical diagnostic testing in general, and in particular, to an apparatus for safely transporting and chilling perishable test samples until analysis of the test samples or until the test samples can be placed in permanent storage.

2. Description of Prior Art

Medical diagnostic tests require that a variety of body fluids and tissues be removed from a patient, often in small quantity, for detailed chemical analysis. Most of these fluids and tissues are perishable, that is, if they are not preserved in a chilled environment they will "spoil" being then unsuitable for the desired analysis. The most common test sample is a blood gas sample. A blood gas sample is arterial blood, from which oxygen ($O_2$), carbon dioxide ($CO_2$) and other gases must be measured.

Where test samples are taken in a laboratory setting, for immediate analysis, no special measures need be taken. However, most test samples, including most blood gas samples, are taken in a setting remote from a laboratory. Such settings may be in a hospital room, in an emergency or accident ward, in a doctor's office, in an ambulance, in a home or even or a battle field. In such instances, the first four among those listed being perhaps the most common, there is an inevitable delay between taking the sample and analyzing the sample. It is simply impractical to have an orderly or special messenger take each test sample in hand and rush it to the laboratory. Firstly, as a matter of efficiency and staff limitations, samples are usually transported together, in groups. Secondly, even where such samples are rushed to a laboratory for analysis, the time of travel is usually such that special measures need be taken to preserve the samples. This is so even when traveling only between floors of the same hospital building.

When samples are to be transported by automobile, truck, airplane and the like, electrically operated refrigerators are usually available. However, for transporting samples within hospitals, and for many of those instances where refrigerators are not available in automobiles and the like, there has been only one means available for preserving and chilling test samples during transport. This one available means has been, and continues to be ice. Further, in order to insure a proper chilling effect, crushed ice or an ice bath is necessary. It is extremely inconvenient to rely on ice, as it must be produced and stored, as it is inherently messy to use and as it is often unweidly to handle. Moreover, in many instances, ice is simply not available, even for inconvenient use.

It is known that when certain chemicals are mixed together, the mixture takes place in an endothermic reaction. An endothermic reaction is driven by heat absorbed from the ambient environment. Such mixtures become cool, and in fact, some become quite cold. An example of such a mixture is water ($H_2O$) and magnesium sulfate ($MgSO_4$), the latter often referred to as Epsom salts. Such mixtures, which form latent refrigerants, have been utilized by hospitals to form artificial "ice" packs. The "ice pack" comprises a plastic bag which has in it a supply of, for example, magnesium sulfate crystals and a supply of water contained in a reservoir within the bag by a rupturable membrane. The membrane is usually broken by slapping the bag on a table top or chair, whereupon the bag may be applied to the body, for example over a bruise. Although such artificial ice packs have been known for some time, they have never been used for any other purpose.

This invention overcomes the difficulties and inconvenience and transporting and preserving test samples by providing an apparatus especially constructed to hold such test samples and surround them with a supply of such a latent refrigerant after activation thereof. In the presently preferred embodiment, the apparatus is adapted to transport and preserve blood gas samples in the syringes by which they are taken, as the syringe is in fact the container in which the blood gas samples are almost always transported. This invention provides, for the very first time, a means for transporting and preserving test samples, such as blood gas, without the need for electrically driven refrigerators and without the need for ice.

An apparatus according to this invention not only provides a chilled environment for test samples, but the fluid in the reservoirs surrounding the test sample provides a cushion and protects against damage. Further, each test sample is individually transported and preserved, so that chances for cross-contamination are reduced. In one embodiment, receiving pockets are formed integrally with the leaf members and membranes. In another embodiment, the leaf members bear a clip member. In either case, the free edges of the leaf members can be held together by strips of adhesive or interlocking teeth. Accordingly, the test sample can be securely in place in a manner which prevents it from accidentally falling out of the apparatus. The outer surfaces of the leaf members can also be provided with gripping strips or portions by which a number of such apparatus can be connected on to another for simultaneous transport.

SUMMARY OF THE INVENTION

It is an object of this invention to provide an apparatus and method for safely transporting perishable test samples.

It is another object of this invention to provide an apparatus and method for safely transporting perishable test samples in a chilled environment.

It is still another object of this invention to provide an apparatus and method for transporting perishable test samples in a chilled environment which apparatus is provided with a self-contained refrigerating means and which method utilizes a self-contained refrigerating means.

It is yet another object of this invention to provide an apparatus as described, which is disposable after a single use.

It is yet another object of this invention to provide an apparatus and method as described, which is particularly adapted for transporting and preserving blood gas samples contained in the syringes by which the samples were drawn.

These and other objects of this invention are accomplished by an apparatus for transporting and preserving perishable test samples, comprising: a pair of substantially flat leaf members foldably connected to one another; membranes disposed on each of the leaf members over a substantial portion thereof, forming reservoirs; a latent refrigerant disposed in the reservoirs; and, means for holding the leaf members together to surround and cushion the test sample, and holding the test sample in heat exchanging relationship with the reservoirs, whereby upon activation of the latent refrigerant the test samples may be safely transported and preserved in a chilled environment. The leaf members and the membranes may be flat except for portions corresponding in shape to the test samples, the portions forming a pocket for receiving a test sample. Alternatively the leaf members may bear a clip member for holding the test sample. The holding means may comprise interlocking members or contact adhesive.

These and other objects are also accomplished by a method for transporting and preserving perishable test samples, comprising the steps of: providing a pair of substantially flat leaf members, foldably connected to one another, with a pair of reservoirs, each extending over a substantial portion of one of the leaf members; filling the reservoirs with a latent refrigerating means; and, after a perishable sample has been taken, activating the refrigerating means; and, surrounding and cushioning the test sample with the reservoirs and holding the test sample in heat exchanging relationship therewith, by closing the leaf members together over the test sample, whereby the test sample may be safely transported and preserved in a chilled environment.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

FIG. 1 is a front perspective view of an apparatus according to this invention in an opened condition;

FIG. 2 is a section view taken along the line II—II in FIG. 1;

FIG. 3 is a section view taken along the line III—III in FIG. 1;

FIG. 4 is a section view taken along the line IV—IV in FIG. 1;

FIG. 5 is a right side elevation of the apparatus of FIG. 1 in a closed condition;

FIG. 6 is a top plan view of FIG. 5;

FIG. 7 is an alternative embodiment of an apparatus according to this invention in an opened condition;

FIG. 8 is a section view taken along the line VIII—VIII in FIG. 7;

FIG. 9 is a section view taken along the line IX—IX in FIG. 7;

FIG. 10 is a section view taken along the line X—X in FIG. 7;

FIG. 11 is a right side elevation of the apparatus of FIG. 1 in a closed condition; and, FIG. 12 is a top plan view of FIG. 11.

DETAILED DESCRIPTION OF THE PREFERRED EMBODIMENTS

An apparatus for transporting and preserving perishable test samples is shown in FIG. 1, and generally designated 10. The perishable test sample is illustrated as a blood gas sample 12 disposed in a syringe 14. The apparatus 10 comprises first and second leaf members 30 and 32. The first and second leaf members may be formed from a single flat member 34 having a fold 36 therein. A first membrane 38 is disposed over one side of first leaf member 30. First membrane 38 extends substantially co-extensively with the first leaf member 30, and is only a bit smaller in area than the leaf member. A second membrane 40, similar in size to the first membrane, is disposed over second leaf member 32. When the first and second membranes are secured to the first and second leaf members, around their perimeters, they define first and second reservoirs 42 and 44. A latent refrigerating means, which can be activated when needed, is stored in each of the reservoirs.

The presently preferred latent refrigerating means are those which rely upon an endothermic reaction as described hereinbefore. The latent refrigerant comprises a charge of a liquid, held in a rupturable container, and a charge of a dry chemical. When the rupturable container is broken, the fluid mixes with the dry chemical and the resulting endothermic reaction immediately chills the fluid as well as anything else in heat exchanging relationship therewith. In accordance with such means, an easily rupturable bag 50 of water is disposed in each reservoir, together with a charge of magnesium sulfate. When the bags 50 are broken, the water mixes with the magnesium sulfate, and becomes a chilled mixture.

It is presently preferred that the apparatus 10 be constructed from relatively strong, but flexible plastic material such as vinyl. The member 34 and the membranes 38 and 40 can be easily cut or punched from flat vinyl stock having a thickness of from 0.004 inches to 0.010 inches in thickness. Such vinyl members can be easily bonded to one another by a heat welding process as is well known in the art of vinyl construction. The first and second membranes 38 and 40 can be attached to the first and second leaf members 30 and 32 by heat welds 46. In order to provide for insertion of the liquid and dry chemical charges of the latent refrigerating means, a section 48 of the heat welds 46 may be held open for such insertion, and then sealed in a subsequent step. The rupturable bags are made from thinner, more brittle plastic material than the leaf members and membranes.

The test sample is preferably disposed in a pocket 54 defined in at least one of the reservoirs, in order to hold the test sample in position within the apparatus. Pocket 54 can be formed in a number of ways. One way is to form such a pocket integrally with one of the leaf members as shown in FIG. 1. This can be accomplished by molding or stretching an appropriate portion of the membrane. A second way is to provide a strap member 56, running over the membrane, which presses the test sample against the reservoir as shown in FIG. 4, and forms a pocket. The strap member 56 can also be attached by heat weld 46 at one or both ends. If only one end is so attached, the other end may be releasably secured by loop and pile fastening strips 58. The strap and integral formation may also be used simultaneously. A third way, which appears similar to the arrangement in FIG. 1, is to make the membrane 38 wider than necessary, at least in part, and attaching the holding strap in such a way as to form a fold in the membrane from the lateral compression. A fourth way for forming the equivalent of a receiving pocket will be explained more fully in conjunction with the embodiment shown in FIGS. 7–12.

This invention is being illustrated in conjunction with the preservation and transportation of blood gas samples. Blood gas samples are most often transported in the syringes by which the samples are taken. Accordingly the receiving pocket 54 is dimensioned in accordance with a typical syringe. Such a typical syringe 14 comprises a hollow cylindrical chamber 16 into which the blood gas sample is drawn by activation of plunger 20. Cylindrical chamber 16 has a shoulder 18 which provides leverage for operation of the plunger. The point of a needle 22 is covered by a cork 24 in order to prevent accidental injury. The cork, together with positioning of the plunger in its down-most position with respect to the blood gas sample, also effectively seals the syringe. If test samples were held in containers of other shapes, it would be a simple matter to provide a pocket having a different shape or dimensions. In a similar fashion, the overall size of the apparatus and reservoirs will be determined by the size of the test samples and the length of time during which the test sample must be maintained in a chilled environment.

It is presently contemplated that the apparatus 10 and syringe 14 will be packaged together as a subsequently disposable kit, perhaps including an alcohol swab as well. One using the kit would remove the syringe, which is provided in sterile condition, and utilizing the alcohol swab provided with the kit, take the necessary blood gas sample. The person would then rupture the fluid bag 50 in each reservoir, by squeezing them, or perhaps by "slapping" them against a table. After the bags have ruptured and the endothermic reaction has begun, the entire syringe can them be placed into the pocket 54, under strap 56. The leaf members can then be folded about fold 36 and the free ends thereof can be held together by a fastening means similar to loop and pile fastening strips 58. It may also be desirable to seal the entire perimeter of the apparatus. This can easily be accomplished by utilizing standard vinyl closing beading 60 which has projecting and interlocking members, which can also be attached by heat welding. When the test sample has been so inserted, and the apparatus has been so sealed, the apparatus will provide a closed, cushioned and sealed environment as shown in FIGS. 5 and 6. Alternatively, strips of contact adhesive may be utilized.

In the embodiment 70 shown in FIG. 7, wherein like numerals refer to like elements in FIG. 1, a U-shaped membrane 72 is disposed on first leaf member 30. The membrane is attached to the leaf member by a weld seam 74, a section 76 of which is held open for insertion of the chemical charges. A clip member 78 having projecting arms 80 is attached to first leaf member 30 by inserting arms 80 through slots 82 formed in the leaf member. The clip member can be permanently attached by a heat weld 84. The arms 80 are provided with apertures 86 into which the syringe can be inserted. In all other respects, the embodiment of FIGS. 7-12 is similar to that of FIGS. 1-6.

In a still further embodiment, not specifically illustrated in the drawings, a clip member similar to clip member 78, but having elongated arms, can be attached to the apparatus 10 of FIG. 1, in place of strap 56, through the area of the fold 36 separating the first and second leaf members. The arms would be long enough to position the syringe, when inserted, in the centers of the reservoirs. It is also possible to arrange the elongated arms and rupturable bags to interengage upon closing the apparatus, automatically rupturing the bags and activating the latent refrigerant. Many such variations are possible, and are contemplated to be within the scope of the invention.

With general reference to the description of the apparatus shown in FIGS. 1-12, a method for transporting and preserving perishable test samples, comprises the steps of: providing at least one of a pair of substantially flat leaf members, foldably connected to one another, with an integrally formed reservoir over a substantial portion thereof; filling the reservoir with a latent refrigerating means; and, after a perishable test sample has been taken, activating the refrigerating means; and, surrounding and cushioning the test sample with the reservoir and holding the test sample in heat exchanging relationship therewith, by closing the leaf members together over the test sample, whereby the test sample may be safely transported and preserved in a chilled environment. The method may further comprise the steps of forming a second reservoir on the other of the leaf members, and filling the second reservoir with a latent refrigerating means.

This invention may be embodied in other specific forms without departing from the spirit or essential attributes thereof, and accordingly, reference should be made to the appended claims, rather than to the foregoing specification, as indicating the scope of the invention.

What is claimed is:

1. An apparatus for transporting and preserving a perishable test sample, comprising:
   a pair of substantially flat leaf members foldably connected to one another;
   a first membrane sealed about its perimeter to at least one of the leaf members, extending over a substantial portion thereof and forming a first reservoir;
   a latent refrigerating means disposed in the reservoir;
   means for positively positioning and securing the test sample in a position flush with the first membrane and therefore the first reservoir, when the apparatus is open, and thereafter, when the apparatus is closed; and,
   means independent of the positioning means for releasably holding the leaf members together to substantially close the entire perimeter of the apparatus and, to thereby surround and cushion the test sample in heat exchanging relationship with the first reservoir, whereby upon activation of the latent refrigerating means, the test sample may be safely enclosed for transportation while preserved in a chilled environment.

2. The apparatus of claim 1, further comprising:
   a second membrane disposed on the other of the leaf members over a substantial portion thereof, forming a second reservoir; and,
   latent refrigerating means disposed in the second reservoir, providing enhanced cushioning and chilling of the test sample.

3. The apparatus of claim 1, wherein each leaf member and the membrane disposed thereon comprise a recessed portion corresponding in shape to the test sample, the portion forming a pocket for receiving the test sample.

4. The apparatus of claim 3, wherein the pocket is formed integrally with the membrane.

5. The apparatus of claim 3, further comprising a strap member spanning one of the membranes, the strap member deforming at least part of the membrane to form the pocket.

6. The apparatus of claim 4, wherein the latent refrigerating means comprises a liquid agent and a dry agent which, when mixed, combine in an endothermic reaction, the liquid mixture also forming a cushion.

7. The apparatus of claim 1, further comprising a clip member carried by one of the leaf members.

8. The apparatus of claim 1, wherein the releaseable holding means for the leaf members comprises a contact adhesive disposed along at least one of the free edges of at least one of the leaf members.

9. The apparatus of claim 1, wherein the releaseable holding means for the leaf members comprises a section of projecting interengagable members disposed along at least one corresponding free edge of each of the leaf members.

10. The apparatus of claim 1, wherein the latent refrigerating means comprises a liquid agent and a dry agent which, when mixed, combine in an endothermic reaction, the liquid mixture also forming a cushion.

11. A method for transporting and preserving perishable test samples in an apparatus having at least one of a pair of substantially flat leaf members, foldably connected to one another, provided with an integrally formed reservoir over a substantial portion thereof, the leaf members having substantially co-extensive free edges when folded together, and the reservoir being filled with a latent refrigerating means, comprising the steps of:
 activating the refrigerating means;
 independently positively positioning and securing the test sample in a position flush with the reservoir when the apparatus is open, and thereafter, when the apparatus is closed;
 surrounding and cushioning the test sample with the reservoir in heat exchanging relationship therewith, by folding the leaf members together over the test sample; and,
 releasably holding the free edges, whereby the test sample may be safely enclosed for transportation while preserved in a chilled environment.

12. The method of claim 11, comprising the steps of: forming a second reservoir on the other of the leaf members; and, filling the second reservoir with a latent refrigerating means.

13. The method of claim 12, further comprising the step of forming a receiving pocket for the test sample in one of the membranes.

14. The method of claim 11, comprising the step of forming the leaf members from parts of a single member divided by a fold.

* * * * *